United States Patent [19]

Matsuo

[11] 4,294,234
[45] Oct. 13, 1981

[54] ENDOSCOPE

[75] Inventor: Kazumasa Matsuo, Hachioji, Japan

[73] Assignee: Olympus Optical Co., Ltd., Tokyo, Japan

[21] Appl. No.: 51,034

[22] Filed: Jun. 22, 1979

[51] Int. Cl.³ ............................................. A61B 1/00
[52] U.S. Cl. .................................... 128/6; 350/96.26
[58] Field of Search ........................................ 128/3–8, 128/9, 303.1, 303.15, 303 A, 326; 350/96.26; 356/241

[56] References Cited

U.S. PATENT DOCUMENTS

| 2,975,785 | 3/1961 | Sheldon | 350/252 X |
| 3,261,350 | 7/1966 | Wallace | 128/6 |
| 3,261,351 | 7/1966 | Wallace | 128/6 |
| 3,456,641 | 7/1969 | Yokota et al. | 128/4 |
| 3,494,354 | 2/1970 | Yokota et al. | 128/6 |
| 3,896,793 | 7/1975 | Mitsui et al. | 128/6 |
| 3,941,121 | 3/1976 | Olinger et al. | 128/6 |
| 3,945,371 | 3/1976 | Adelman | 128/6 X |

FOREIGN PATENT DOCUMENTS

| 964567 | 7/1964 | Canada | 128/6 |
| 2545761 | 4/1977 | Fed. Rep. of Germany | 128/303.15 |
| 2800607 | 10/1978 | Fed. Rep. of Germany | 128/4 |
| 1560249 | 6/1967 | France | 128/6 |

Primary Examiner—Robert W. Michell
Assistant Examiner—Arthur S. Rose

[57] ABSTRACT

A pipe-like extension guide is inserted into a control section housing (operation section) through an insertion hole in the side wall of the control section housing connected to the base end of an elongated sheath. An elongated cut out is formed in the side wall of the inserted end portion of the extension guide, and the base end portion of an optical fiber bundle for observation is introduced through the cutout into the extension guide such that the end face of the bundle aligns with an eyepiece held in an eyepiece section which is fitted over the guide. The end surface of the extension guide is intimately abutted against the inner wall of the housing.

5 Claims, 4 Drawing Figures

F I G. 3
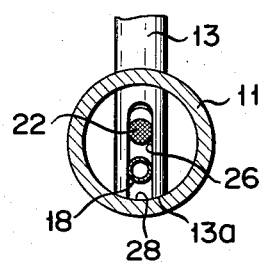
F I G. 4
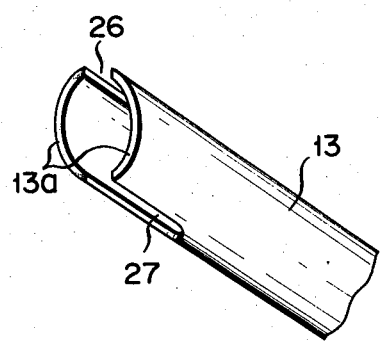

ENDOSCOPE

BACKGROUND OF THE INVENTION

This invention relates to an endoscope of the type in which a channel tube for inserting a body-cavity treating instrument such as a catheter therein is disposed in a sheath and the base end of the tube extends through the rear end wall of a control section housing, of which the front end is attached to the sheath.

As an endoscope having the above-mentioned channel tube a laparoscope etc. can be listed. As such body-cavity treating instrument use is often made of a generally straight, unyielding one. It is desirable from the viewpoint of operation that a channel for inserting the instrument therein be straight. A channel tube is formed such that it extends straight along the length of the sheath from a control section housing where a manual operation is effected. The base end portion of the channel tube extends through the rear end wall of the control section housing to provide an instrument inserting hole. In the endoscope of this type an optical fiber bundle is disposed in the sheath, but there is no ample room for an eyepiece section to be provided at rear end of the control section housing, the eyepiece section and optical fiber bundle constituting part of an observation system. For this reason, the eyepiece section is provided at the side section of the housing and, for example, a prism is provided to permit an optical axis of the observation system to be bent. In this method, however, a higher degree of skill is required from the standpoint of assembly in adjusting the position of a prism and, moreover, the misalignment of the optical system tends to occur from the structural viewpoint, failing to obtain a proper optical performance. From this viewpoint, a specific manufacturing technique is required in the assembly of endoscopes and it is also difficult to mass-produce. Thus, production problems are encountered in the prior art.

SUMMARY OF THE INVENTION

This invention provides an endoscope free from the above-mentioned drawbacks, which is simple in construction, durable and high in performance and can be easily assembled without requiring a higher degree of skill in the adjustment of an observation optical system and without involving a problem such as the misalignment of an observation optical system. In order to attain the object of this invention an insertion hole is provided at the side surface of a control section housing, a pipelike extension guide is slantwise inserted into a housing through said insertion hole such that an eyepiece section is fitted over the outer free end of the extension guide, an opening means such as an elongated or axial cutout is provided in that portion of the extension guide which is inserted into the housing, and a base end portion of an optical fiber bundle is inserted through said opening means into the guide such that the end face of the inserted end portion of the optical fiber bundle aligns with, and faces, an eyepiece. The base end portion of the optical fiber bundle is guided by the extension guide such that it extends sideway of the control section housing.

In this arrangement, the base end portion of the fiber bundle extends such that it confronts the eyepiece, and thus no prism is necessary. An assembly of an optical system can be readily made merely by inserting the base end portion of the fiber bundle into the guide. In this case, no particular adjustment is necessary and no misalignment problem of the optical system is also involved.

In the preferred embodiment of this invention opening means is constructed of an elongated axial cutout (first cutout) which is opened at the inserted end of the extension guide. The width of the cutout is made substantially equal to the diameter of the optical fiber bundle. Since both the sides of the cutout hold the fiber bundle in place, the fiber bundle is held stably in position. That end of the extension guide which is inserted into the housing is abutted against the inner surface of the control section housing such that it conforms to the inner surface of the control section. Thus, the inserted guide is held stably in place. From this viewpoint, assembly is easily made.

Further, an elongated axial cutout (second cutout) is also provided in the inserted end portion of the guide such that it faces the above-mentioned elongated axial cutout (first cutout) across the diameter of the guide and opened at the inserted end. The base end portion of the channel tube is frictionally inserted through the first and second cutouts and held there. It is preferred that the width of the second cutout be substantially equal to the diameter of the channel tube.

In the above-mentioned arrangement the extension guide and channel tube can be arranged in the control section housing without interference. Since the channel tube is held on both the sides edges of each of the cutouts, it occupies a stable position. Both the cutouts are opened at the inserted end of the guide and thus it is easy to insert the channel tube into the cutouts. During the assembly of the guide into the housing the operator can easily insert the channel tube through the cutouts without any particular operation.

BRIEF DESCRIPTION OF THE DRAWINGS

This invention will be further described by way of example by referring to the accompanying drawings in which:

FIG. 3 is a cross-sectional view as taken along line 3—3 of FIG. 2; and

FIG. 4 is a perspective view showing an enlarged essential part of an extension guide as shown in FIG. 2.

DETAILED DESCRIPTION OF THE PREFERRED EMBODIMENT

Figure 1:
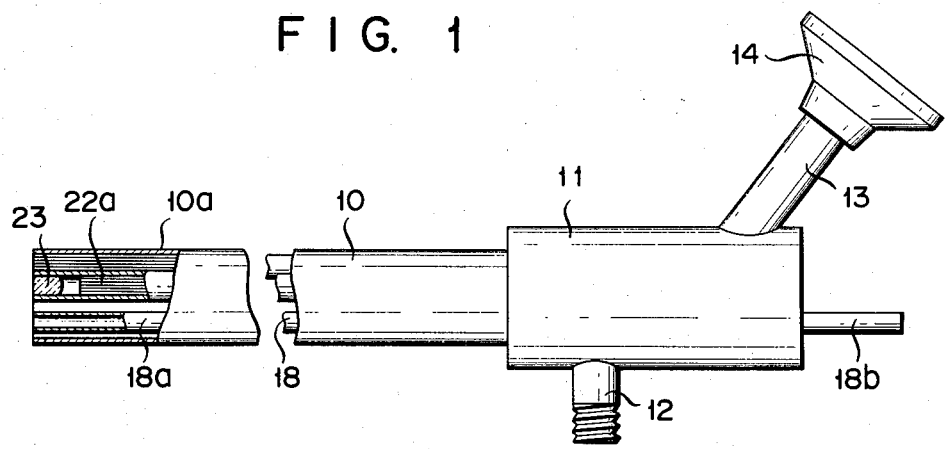
FIG. 1 is an outer view, partially broken away, showing an endoscope according to the embodiment of this invention.

In FIG. 1 an endoscope of this invention is a socalled laparoscope of which an elongated cylindrical sheath 10 with a whole length of about 30 cm is rigid and straight. The base end of the sheath 10 is rigidly connected to one end (forward end) of a control section housing 11 which is cylindrical in configuration. The housing 11 is the control section where the operator performs a manual operation. A connector 12 for connection to a power supply (not shown) for illumination is attached to the side of the housing 11 and a pipelike extension guide 13 as will be later described is inserted into, and fixed to, the side of the housing 11. An eyepiece section 14 is provided at the external free end of the guide 13. The eyepiece section 14 comprises an eyepiece 15 (FIG. 2), a cover glass 16 for covering the eyepiece and an eyepiece cover 17 mounted on the outer free end of the guide 13 to support the eyepiece 15 and cover glass 16.

The operator manually operates the sheath 10 at the control section 11. The sheath 10 is inserted into, for example, the body cavity of a human being (patient) and a region of interest (ROI) of the body cavity is observed through the eyepiece section 14.

A channel tube 18 is disposed within, the along the axis of, the sheath 10 and the distal end 18a of the channel tube 18 is opened at the distal end portion of the sheath 10. The other end, i.e. the base end 18b, of the channel tube 18 extends straight into the housing 11 and through hole 19 in the rear wall of the housing 11 into the outside. An instrument such as a catheter can be inserted into a channel 20 of the tube 18 through the base end of the channel tube 18. The channel tube 18 is made of a metal or a rigid synthetic resin. The tube 18 is held by a proper means, not shown, within the sheath 10, but this means belongs to a known art.

A straight guide pipe 21 for an optical fiber bundle 22 to be later described, together with the tube 18, is inserted into the sheath 10 over a length of the sheath 10 and the base end portion of the guide pipe 21 extends a smaller distance into the housing 11. The guide pipe 21, like the tube 18, is held by a proper means, not shown, within the sheath 10. The guide pipe 21 is made of a metal or a rigid synthetic resin.

The above-mentioned optical fiber bundle 22 constituting one of an observation system is inserted through the guide pipe 21. The distal end 22a of the bundle 22 is located in the distal end 10a of the sheath 10 and optically leads to the outside through a lens 23. The base end portion 22b of the fiber bundle 22 extends behind the guide pipe 21 and, as will be later described, inserted into the extension guide 13. The fiber bundles 22 are comprised of a number of thin optical glass fibers. In this embodiment use is made of a fiber bundle whose fibers are united together in a glass rod-like form over a whole length. A variety of fiber bundle manufacturing methods have been proposed up to date. Though the manufacturing method does not constitute the subject matter of this invention, the structure of the fiber bundle used in the embodiment of this invention will be briefly explained below.

A rigid fiber bundle is formed by covering a bundle of thin glass fibers with a glass material such as an acid-soluble glass and drawing it under heating into a glass rod-like form. The flexible portion of the fiber bundle is provided by dipping a desired fiber bundle portion in an acid such as nitric acid to solve the covered glass material. In this embodiment such a glass rod-like fiber bundle is used. During the bundle manufacturing process the fibers of the base end portion 22b of the bundle are united together in the bent state. The end faces of the bundle are polished. Since even such rigid bundle 22 has some flexibility no obstacle is involved in the insertion of the bundle through the sheath 10 and through the extension guide 13.

A light conducting fiber bundle 24 for illumination is inserted into the sheath 10 and extends from the connector 12 to the distal end 10a of the sheath 10. This structure belongs to the prior art and further explanation thereof is omitted for brevity. As shown in FIG. 3 the connector 12 is connected to an external power source through a code as indicated by a dot-dash line in FIG. 1.

The pipe-like extension guide 13 is formed of, for example, a metal pipe and inserted into the housing 11 through an inclined hole 25 in the cylindrical side wall 11b of the housing 11. This insertion is effected when the endoscope is assembled. The inclined hole 25 is formed such that its axis is inclined with respect to the side wall 11b of the control housing 11. The guide 13 is attached to the housing 11 such that it is set at a predetermined inclination angle with respect to the side wall 11b of the housing 11. The inclination angle is properly selected at the design stage.

An axial slot or cutout 26 is formed in the side wall of that end portion of the extension guide which is inserted into the housing 11. The axial slot 26 is opened at the inserted open end of the extension guide 13 and provides an opening means. An axial slot or cutout 27 is also formed in the side wall of said end portion of the extension guide 13 so as to face the axial slot 26 across the diameter of the extension guide 13. The axial slot 27 is opened at the open end of the guide 13.

In this embodiment the fiber bundle 22 and channel tube 18 have substantially the same diameter. The cutout 26 has a width substantially the same as that of the fiber bundle 22. The width of the cutout 27 is substantially the same as that of the tube 18. Where the tube 18 is made of a metal it is preferred that the widths of the cutouts 26, 27 be somewhat greater than the diameter of the tube 18. The configuration of the cutouts will be understood from FIG. 3 in particular. The inserting end portion of the extension guide 13 is so tapered as to be kept in intimate contact with the inner side wall surface 28 of the housing with the inner open end thereof curved to conform to the cylindrical inner wall surface of the housing. The configuration of the open end 13a of the extension guide 13 will be well understood from FIGS. 2 and 3.

Figure 2:
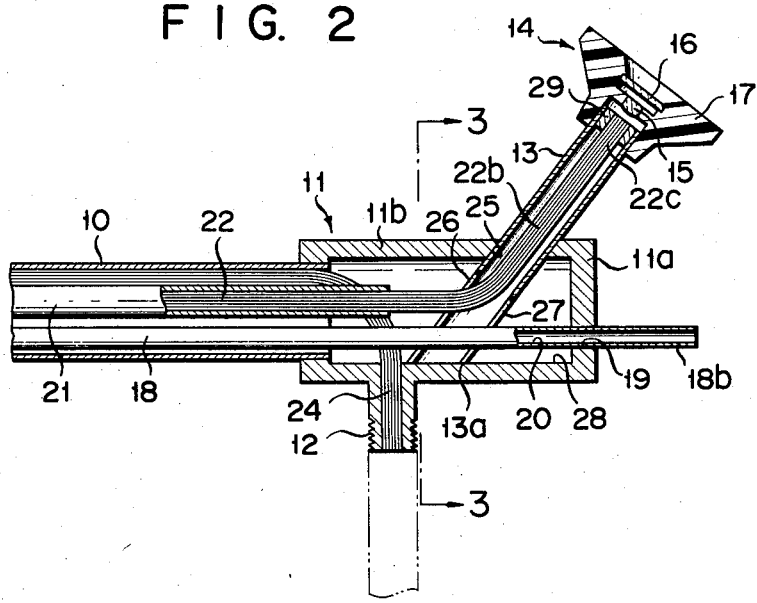
FIG. 2 is a longitudinal cross-section showing an essential part of FIG. 1.

Upon assembly, the base end portion 22b of the optical fiber bundle is drawn out of the housing 11. When the extension guide 13 is inserted into the hole 25 the base end portion 22b of the optical fiber bundle is inserted through the cutout 26 into the guide 13. The extension guide 13 is inserted though the hole 25 into the housing 11 such that the inserting end, i.e. the inner open end, of the extension guide 13 is snugly abutted against the inner wall surface 28 of the housing. During this process the base end portion of the channel tube 18 is inserted through the cutouts 26, 27 of the extension guide 13. By so doing, the channel tube 18 is frictionally engaged with both the side edges of the cutouts 26, 27 of the extension guide 13 and supported in that position as shown in FIG. 2. As a result, the base end portion of the tube 18 is prevented from drifting within the housing 11.

At this stage of assembly, the outer free end of the extension guide 13 is in the open state and the eyepiece section 14 is not yet fitted there. The base end 22c of the fiber bundle 22 is held in a retainer ring 29 which is attached in the open free end portion of the extension guide 13. By so doing, the base end portion 22b of the fiber bundle occupies the position as shown in FIG. 2. Since the width of the cutout 26 is substantially equal to the diameter of the bundle 22 the bundle 22 is frictionally contacted with both the side edges of the cutout 26 and takes the position as shown in FIG. 2. Thus, the base end portion of the bundle 22 is restricted against unauthorized movement within the housing 11 and guide 13.

Then, the eyepiece section 14 is fitted over the outer free end portion of the guide 13 such that an eyepiece 15 is aligns with, and faces, the base end 22c of the fiber bundle 22. The eyepiece 15 and base end 22c of the fiber bundle 22 are optically directly connected with no prism etc. interposed therebetween.

The inserted extension guide 13 is rigidly secured around the hole 25 in the housing (i.e. in the position as shown in FIG. 2) by a means such as welding, soldering and brazing. Since the elongated extension guide 13 is rigidly secured around the hole 25 i.e. in the intermediate position thereof with the inner open end of the guide 13 snugly abutted against the inner wall surface 28 of the housing 11, the guide 13 is very positively attached to the housing 11. The frictional engagement of the channel tube 18 and fiber bundle 22 with the cutouts 26 and 27, respectively, contributes also to the stabilization of the guide 13.

When the extension guide 13 is sufficiently attached around the mounted hole 25 in the housing 11, no strength problem arises even if the inserting end of the guide is not abutted against the inner surface 28 of the housing. In this case, the inserting end of the guide may be fixed around the mounting hole in the housing without being inserted into the housing or may be inserted halfway into the housing. In this modification the opening of the inserting end of the guide can be used in place of the opening means (cutout 26) through which the base end portion of the fiber bundle is inserted. Such modification is included in this invention, but the construction as shown in the Figures is more preferable. As a fiber bundle use is made of the above-mentioned fiber bundles whose fibers are united together in the glass rod-like form over the whole length. By so doing, the breakage of the thin glass fibers in the bundle is decreased to a minimum possible extent, thus improving the durability of the bundle.

In this way, the extension guide 13 is readily assembled in the housing 11. After assembly, the guide 13 is positively attached to the housing 11 and no adjustment of the observation system is necessary. The guide per se has a unique function of holding the fiber bundle and channel tube in place by the means such as cutouts.

What is claimed is:

1. An endoscope comprising:
   an elongated rigid sheath to be inserted into a body cavity, said sheath having a base end and a distal end;
   a control section housing having a side wall and an end wall connected to the base end of the sheath;
   a rigid channel tube inserted within the sheath along the length of the sheath to permit an instrument such as catheter to be inserted therein, said channel tube having a base end extended into the housing and a distal end opened at the distal end of the sheath;
   an insertion hole formed in the side wall of said control section housing;
   an extension guide having an outer free end and an inserted end slantwise inserted into the housing through the insertion hole;
   an eyepiece fitted over the outer free end of the extension guide;
   an optical fiber bundle having a straight portion disposed in the sheath, a distal end extended in the distal end of the sheath, a base end portion bent relative to the straight portion, and a base end, said bundle being made rigidly in the glass rodlike form over substantially the whole length; and
   opening means mounted on the inserted end of the extension guide for introducing the base end portion of the fiber bundle into the insertion guide, so that said base end of the fiber bundle is optically coupled to the eyepiece, said opening means comprising an elongated cut out formed in said extension guide along the axial direction thereof and opened at the inserted end of the extension guide.

2. An endoscope according to claim 1 in which said cutout has a width substantially equal to the diameter of said optical fiber bundle.

3. An endoscope according to claim 1 or claim 2 in which the inserted end of said extension guide is formed such that an end surface of the inserted end intimately conforms to the inner wall surface of the housing.

4. An endoscope according to claim 1 in which an elongated second cutout is formed in the the inserted end of said extension guide so as to face the first elongated cutout across the diameter of the extension guide, said elongated second cutout being opened at the open end of the guide, said channel tube being inserted through the cutouts.

5. An endoscope according to claim 4 in which each of said first and second cutouts has a width substantially equal to the diameter of said channel tube.

* * * * *